United States Patent
Maindron et al.

(10) Patent No.: US 12,398,354 B2
(45) Date of Patent: Aug. 26, 2025

(54) CULTURE PLATE

(71) Applicants: Commissariat à l'Énergie Atomique et aux Énergies Alternatives, Paris (FR); Institut National Polytechnique de Grenoble, Grenoble (FR); Centre National de la Recherche Scientifique, Paris (FR)

(72) Inventors: Tony Maindron, Grenoble (FR); Franz Bruckert, Grenoble (FR); Marianne Weidenhaupt, Grenoble (FR)

(73) Assignees: Commissariat à l'Énergie Atomique et aux Énergies Alternatives, Paris (FR); Institut National Polytechnique de Grenoble, Grenoble (FR); Centre National de la Recherche Scientifique, Paris (FR)

( * ) Notice: Subject to any disclaimer, the term of this patent is extended or adjusted under 35 U.S.C. 154(b) by 628 days.

(21) Appl. No.: 17/345,154

(22) Filed: Jun. 11, 2021

(65) Prior Publication Data
US 2021/0388300 A1    Dec. 16, 2021

(30) Foreign Application Priority Data
Jun. 12, 2020    (FR) ...................................... 2006151

(51) Int. Cl.
   *C12M 1/32*    (2006.01)
   *C12M 1/00*    (2006.01)
   *H05B 33/02*    (2006.01)

(52) U.S. Cl.
   CPC ............ *C12M 23/12* (2013.01); *C12M 23/20* (2013.01); *C12M 23/22* (2013.01); *C12M 31/10* (2013.01); *H05B 33/02* (2013.01)

(58) Field of Classification Search
   CPC ...... C12M 23/12; C12M 23/20; C12M 23/22; C12M 31/10; H05B 33/02
   USPC ....................................................... 435/305.2
   See application file for complete search history.

(56) References Cited

U.S. PATENT DOCUMENTS

| 7,977,089 B2 * | 7/2011 | Wikswo ................. C12M 41/00 435/297.5 |
| 10,392,596 B2 | 8/2019 | Chung et al. |
| 2007/0292837 A1 * | 12/2007 | Deutsch ................ B29C 65/002 435/174 |
| 2016/0216192 A1 * | 7/2016 | Gu ..................... G01N 15/1468 |

(Continued)

FOREIGN PATENT DOCUMENTS

| CN | 108102918 A | 6/2018 |
| CN | 208271901 U | 12/2018 |

(Continued)

OTHER PUBLICATIONS

JP-2010158185-A Machine English Translation (Year: 2010).*

(Continued)

*Primary Examiner* — Michael L Hobbs
*Assistant Examiner* — Lenora A Abel
(74) *Attorney, Agent, or Firm* — Wolf, Greenfield & Sacks, P.C.

(57) ABSTRACT

A culture plate including: an array of light sources formed inside and on top of a semiconductor substrate; a transparent planarization layer coating the array of light sources; and an array of wells formed on said layer, each light source being located vertically in line with a well.

13 Claims, 4 Drawing Sheets

(56) References Cited

U.S. PATENT DOCUMENTS

2017/0362561 A1* 12/2017 Chung .................. C12M 21/02
2020/0032192 A1    1/2020 Zhou

FOREIGN PATENT DOCUMENTS

| EP | 2 690 167 A1 | | 1/2014 | |
|----|---|---|---|---|
| JP | 2010158185 A | * | 7/2010 | ............ C12M 23/52 |
| WO | WO 2016/108049 A1 | | 7/2016 | |
| WO | WO 2020/091732 A1 | | 5/2020 | |

OTHER PUBLICATIONS

Preliminary Search Report for French Application No. 2006151, dated Feb. 19, 2021.
Stuede et al., Controlling the behavior of single live cells with high density arrays of microscopic OLEDs. Advanced Materials. Dec. 2015;27(46):7657-61.

* cited by examiner

CULTURE PLATE

CROSS-REFERENCE TO RELATED APPLICATION

This application claims priority to French Patent Application 2006151, filed Jun. 12, 2020, the contents of which is incorporated herein by reference in its entirety.

TECHNICAL BACKGROUND

The present disclosure generally concerns electronic devices and, more particularly, devices of stimulation of cells with light.

PRIOR ART

In fields such as optogenetics, light sources associated with a microscope are often used to illuminate cultured cells. Tissues of living organisms may alternately be illuminated due to optical fibers coupled to a light source. Tools coupled with microscopy, which allow a spatial addressing of the emitted light, are further known. Current illumination devices however remain limited, particularly in terms of illuminated surface area and of illumination parameters capable of being tested in parallel.

SUMMARY

There is a need to improve current cell illumination devices and methods of manufacturing the same.

An embodiment overcomes all or part of the disadvantages of known cell illumination devices and methods of manufacturing the same.

An embodiment provides a culture plate comprising:
an array of light sources formed inside and on top of a semiconductor substrate;
a transparent planarization layer coating the array of light sources; and
an array of wells formed on said layer, each light source being located vertically in line with a well.

According to an embodiment, said layer is made of a photocrosslinkable organosilicon material.

According to an embodiment, said layer has a thickness in the range from 1 µm to 10 µm.

According to an embodiment, the well array is made of polydimethylsiloxane.

According to an embodiment, each light source comprises at least one organic light-emitting diode.

According to an embodiment, each light source comprises a diode intended to emit white light.

According to an embodiment, each diode is individually controllable.

According to an embodiment, each light source comprises three diodes intended to respectively emit red light, green light, and blue light.

According to an embodiment, the array of light sources is located on the side of a first surface of the substrate, opposite to a second surface of the substrate comprising connection pads.

According to an embodiment, the connection pads are connected to the first surface of the substrate by through vias.

According to an embodiment, each light source comprises a control circuit independent from the other light sources.

According to an embodiment, the bottom and/or the lateral walls of at least a portion of the wells of the array are functionalized.

An embodiment provides a method of manufacturing a plate such as described.

According to an embodiment, the method comprises the steps of:
forming the array of light sources inside and on top of the semiconductor substrate;
coating the array of light sources with the transparent planarization layer; and
forming at the surface of said layer a well vertically in line with each light source.

BRIEF DESCRIPTION OF THE DRAWINGS

The foregoing and other features and advantages of the present invention will be discussed in detail in the following non-limiting description of specific embodiments and implementation modes in connection with the accompanying drawings, in which.

DESCRIPTION OF THE EMBODIMENTS

Like features have been designated by like references in the various figures. In particular, the structural and/or functional elements common to the different embodiments and implementation modes may be designated with the same reference numerals and may have identical structural, dimensional, and material properties.

For clarity, only those steps and elements which are useful to the understanding of the described embodiments and implementation modes have been shown and will be detailed. In particular, the organic light-emitting diodes and their manufacturing methods are not detailed, the embodiments and implementation modes being compatible with current organic light-emitting diodes and methods of manufacturing the same.

Unless indicated otherwise, when reference is made to two elements connected together, this signifies a direct connection without any intermediate elements other than conductors, and when reference is made to two elements coupled together, this signifies that these two elements can be connected or they can be coupled via one or more other elements.

In the following description, when reference is made to terms qualifying absolute positions, such as terms "front", "rear", "top", "bottom", "left", "right", etc., or relative positions, such as terms "above", "under", "upper", "lower", etc., or to terms qualifying directions, such as terms "horizontal", "vertical", etc., it is referred unless specified otherwise to the orientation of the drawings or to a culture plate in a normal position of use.

Unless specified otherwise, the expressions "around", "approximately", "substantially" and "in the order of" signify within 10%, and preferably within 5%.

The term transmission factor (or "transmittance") of a layer designates the ratio of the intensity of the radiation coming out of the layer to the intensity of the radiation entering the layer. In the following description, a layer is said to be opaque to a radiation when the transmission factor of the radiation through the layer is smaller than 10%. In the following description, a layer is called transparent to a radiation when the transmission factor of the radiation through the layer is greater than 10%.

The term reflection factor (or "reflectance") of a layer designates the ratio of the light flow reflected by the layer to the light flow incident on the layer. In the following description, a layer is called reflective when the reflection factor of the layer is greater than 90%.

Figure 1:
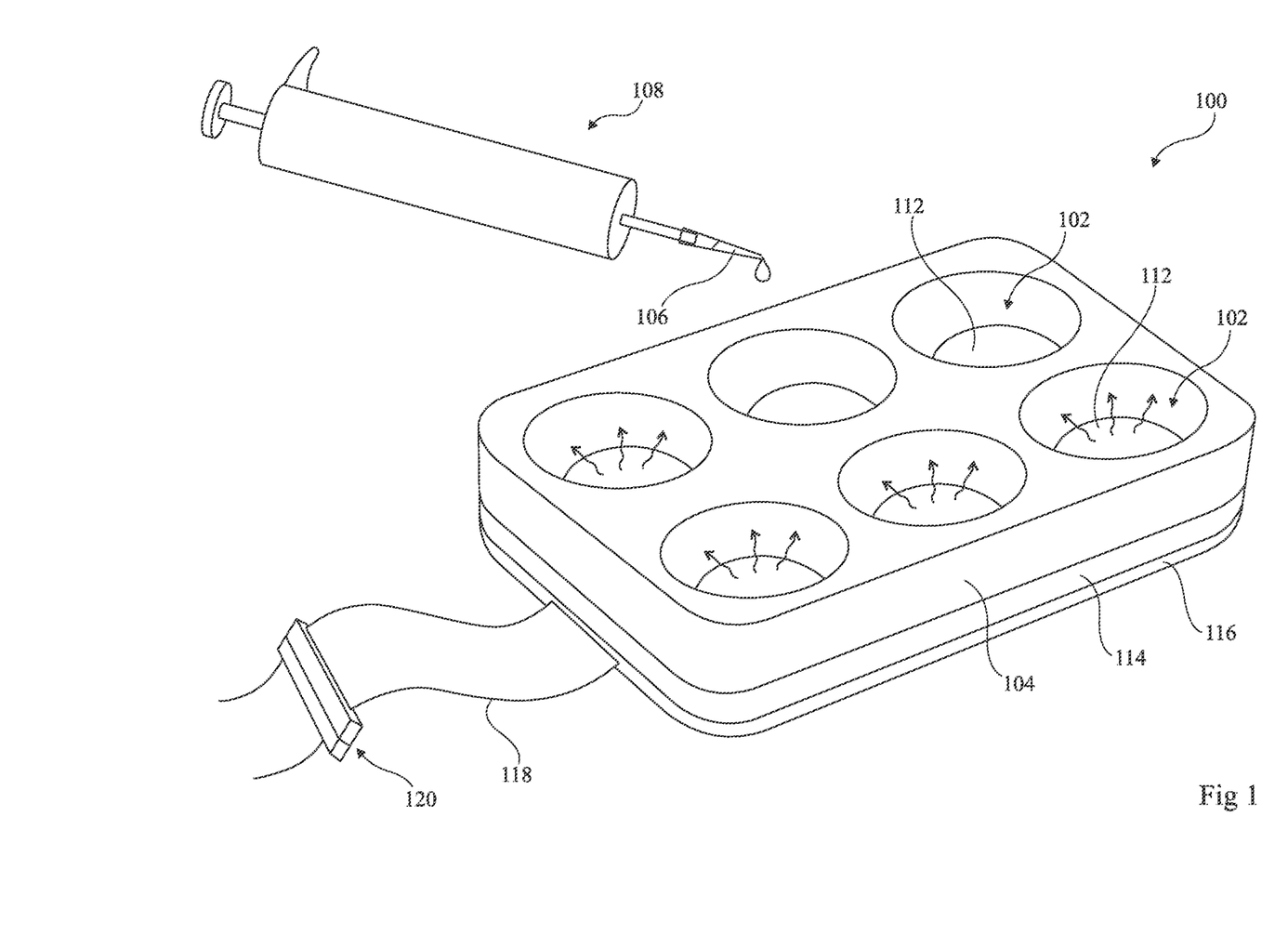
FIG. 1 is a partial simplified perspective view of an embodiment of a multi-well culture plate.

FIG. 1 is a partial simplified perspective view of an embodiment of a multi-well culture plate or plate 100.

Culture plate 100 comprises an array of wells 102. In the shown example, each well 102 has a cylindrical shape (of circular cross-section, in top view) vertically extending from the upper surface of plate 100. Wells 102 are for example regularly distributed on the upper surface of plate 100. As an example, all the wells 102 of plate 100 have identical dimensions, to within manufacturing dispersions.

In the shown example, the wells 102 of plate 100 are recesses or compartments formed inside of a layer 104. Wells 102 are for example intended to contain a biological substance (or medium) 106 for example comprising cells. As an example, biological substance 106 is dispensed into the wells 102 of plate 100 by means of a pipette 108 equipped with an adapted pipette tip adapted, for example, to the dimensions of wells 102.

Layer 104 is preferably made of a biocompatible material, in other words of a material which is non-toxic for the cells contained in biological substance 106. As an example, layer 104 is made of polydimethylsiloxane (PDMS) or of a plastic polymer, for example, made of polystyrene, of polypropylene, of polycarbonate, etc. Layer 104 may be coated with a chemical functionalization intended to favor an adhesion of the cells contained in substance 106. For example, the bottom and/or the lateral walls of at least a portion of wells 102 are functionalized.

Culture plate 100 further comprises an array of light sources 112. In the shown example, the array of light sources 112 is vertically aligned with respect to the array of wells 102. Each light source 112 is more precisely located vertically in line with a well 102 to which it is associated. As an example, the bottom of each cell 102 is centered with respect to the upper surface of the associated light source 112.

In the shown example, the array of light sources 112 is coated on all its lateral surfaces with a layer 114. As an example, layer 114 enables to protect against oxidation contacting elements (not shown) associated with light sources 112. Layer 114 is for example a so-called underfill layer made of a biocompatible material. As an example, layer 114 is made of epoxy resin or glue, for example, the glue known under trade name "Epo-Tek MED-375".

The light sources 112 of plate 100 are for example powered and controlled via a printed circuit board 116. In the shown example, board 116 is located on the lower surface side of plate 100, that is, the surface opposite to the array of wells 102. Board 116 is for example coupled or connected to a control unit (not shown in FIG. 1), for example, via a ribbon cable 118 and a connector 120. As an example, the control unit is a computer configured to supply the electric power and to control parameters of illumination of the light sources 112 of culture plate 100.

According to an embodiment, the light sources 112 of culture plate 100 are individually addressable. Each light source 112 may in particular emit or not light independently from the other light sources 112 of plate 100. As an example, each light source 112 comprises a control circuit (not shown) which is specific thereto, that is, a control circuit independent from the control circuits of the other light sources 112 of plate 100.

In FIG. 1, the emission of light originating from a light source 112 has been symbolized by arrows starting from the upper surface of the considered light source 112 and oriented towards the inlet of the associated well 102. In the shown example, it is arbitrarily assumed that four light sources 112 emit light while two light sources 112 emit no light.

The illumination parameters of each light source 112 are preferably adjustable independently from the illumination parameters of the other light sources 112 of plate 100. As an example, it is now possible to individually control, that is, for each light source 112 of plate 100, parameters selected from among:
  an illumination duration;
  an emission wavelength or wavelength range, in other words an emitted color;
  a luminance or emission power level; and
  an emission mode, for example continuous or in pulsed light, it being for example possible to alternate the continuous and pulsed light emission modes during a same phase of exposure of a well 102.

Generally, culture plate 100 enables to control the illumination conditions within each well 102. It may in particular be chosen to illuminate or not the biological substance 106 contained in each well 102 of plate 100 and to individually control the emission parameters of each light source 112 in operation.

An advantage of culture plate 100 lies in the fact that it is possibly to vary, from one well 102 to the other, the illumination conditions to which biological substance 106 is submitted. In applications such as studies of cell response to light, optogenetics, neuromodulation, neuroprotection, diagnosis, and sequencing, the use of plate 100 for example enables to advantageously simplify the implementation of designs, in particular relating to the use of culture plates or plates having all their wells exhibiting similar illumination conditions.

Another advantage of culture plate 100 lies in the fact that the materials of its external surfaces are for example compatible with methods of sterilization with ultraviolet light or with a gas, for example, ethylene oxide. As an example, this enables to reuse a same plate 100 to perform experiments implementing different biological substances.

Although FIG. 1 shows an embodiment where culture plate 100 comprises six wells 102, plate 100 may in practice comprise any number of wells 102, for example, four, eight, twelve, twenty-four, forty-eight, or ninety-six wells 102. Further, although FIG. 1 shows a culture plate 100 comprising wells 102 of cylindrical shape, plate 100 may in practice comprise wells 102 of any shape, for example, wells 102 having, in top view, a cross-section of rectangular or square shape.

As an example, each well 102 has:
- a maximum dimension (in top view) in the order of from a few micrometers to a few millimeters, for example, in the range from 5 mm to 40 mm; and
- a depth in the range from 100 μm to 30 mm, for example, in the range from 10 mm to 20 mm.

Each well 102 for example has:
- a surface (in top view) in the range from 0.19 cm$^2$ to 13 cm$^2$, for example, equal to approximately 0.3 cm$^2$ for a plate 100 comprising ninety-six wells 102; and
- a volume in the range from a few microliters to a few milliliters, for example in the range from 0.1 mL to 20 mL, for example, equal to approximately 0.3 mL for a plate 100 comprising ninety-six wells 102.

FIGS. 2 to 7 hereafter illustrate structures obtained at the end of successive steps of an example of an implementation mode of a method of manufacturing the multi-well culture plate 100 of FIG. 1.

Figure 2:
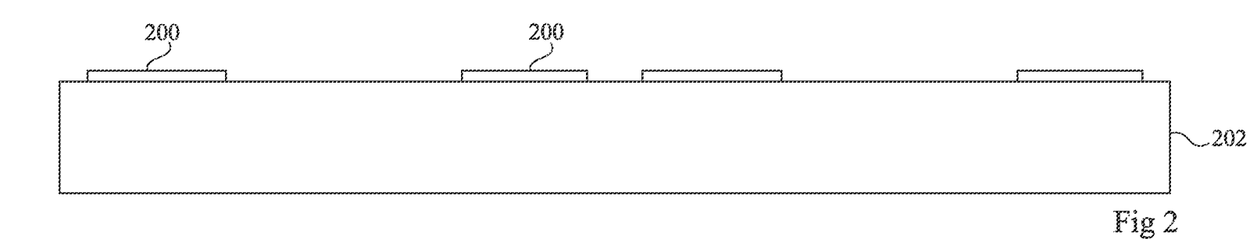
FIG. 2 is a partial simplified cross-section view illustrating a step of an implementation mode of a method of manufacturing the culture plate of FIG. 1.

FIG. 2 is a partial simplified cross-section view illustrating a step of the implementation mode of the method of manufacturing the culture plate 100 of FIG. 1.

During this step, power supply and addressing circuits 200 are formed inside and on top of a semiconductor substrate 202.

As an example, substrate 202 is a wafer or a piece of wafer made of a semiconductor material, for example, of silicon. In the orientation of FIG. 2, power supply and addressing circuits 200 are formed on the upper surface or front surface side of substrate 202. These circuits are in particular intended to enable to individually control each light source 112 (FIG. 1) of plate 100. As an example, each light source 112 is associated with a control circuit 200 distinct from the control circuits 200 of the other light sources 112 of plate 100.

Figure 3:
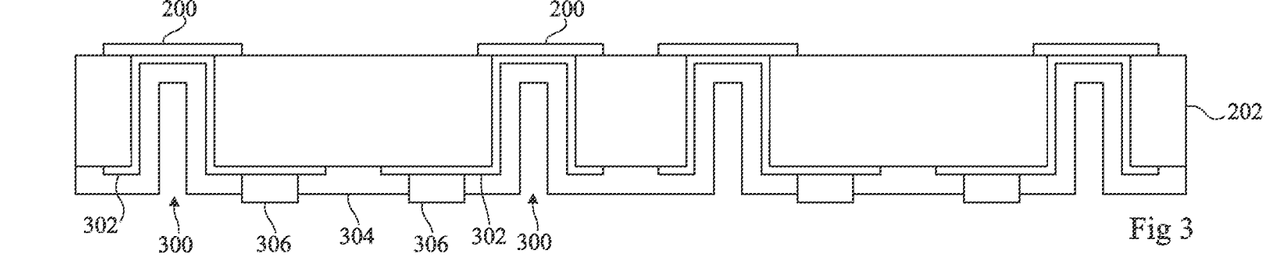
FIG. 3 is a partial simplified perspective view illustrating another step of the implementation mode of the method of manufacturing the culture plate of FIG. 1.

FIG. 3 is a partial simplified cross-section view illustrating another step of the implementation mode of the method of manufacturing the culture plate 100 of FIG. 1, formed from the structure such as described in relation with FIG. 2.

During this step, substrate 202 is thinned and vias 300 are formed.

As an example, the thinning of substrate 202 is performed by grinding on the side of the surface of substrate 202 which does not comprise power supply and addressing circuits 200 (in other words, the lower surface of substrate 202, in the orientation of FIG. 3). At the end of this operation, substrate 202 for example has a thickness in the range from 50 μm to 150 μm, preferably from 70 μm to 100 μm.

In the shown example, vias 300 cross substrate 202 across its entire thickness. Vias 300 for example enable to transfer onto the lower surface of substrate 202 contacting elements of the circuits 200 located on the upper surface side of substrate 202.

The lateral walls and the bottom of through vias 300 are for example coated with portions 302 of an electrically-conductive layer, for example, a copper layer. In the shown example, each conductive layer portion 302 continues horizontally on top of and in contact with the lower surface of substrate 202, in the vicinity of the corresponding via 300.

In practice, the conductive layer is for example deposited all over the structure on the lower surface side of substrate 202. As an example, conductive layer portions 302 are then formed by etching.

Substrate 202 further comprises, on its lower surface side, an electrically-insulating layer 304. Layer 304 covers free areas of the lower surface of substrate 202, and coats conductive layer portions 302 except for regions on top of and in contact with which connection pads 306 are formed.

In practice, insulating layer 304 is for example first deposited all over the structure on the lower surface side of substrate 202. As an example, openings are then formed in layer 304 to expose regions intended to receive connection pads 306. Pads 306 are finally formed vertically in line with the regions which are not coated with insulating layer 304.

Although this is not shown, another insulating layer may be formed on the structure, on the lower surface side of substrate 202, prior to the deposition of the conductive layer. In this case, this layer is for example intended to ensure a function of electric insulation between conductive layer portions 302 and substrate 202.

Figure 4:
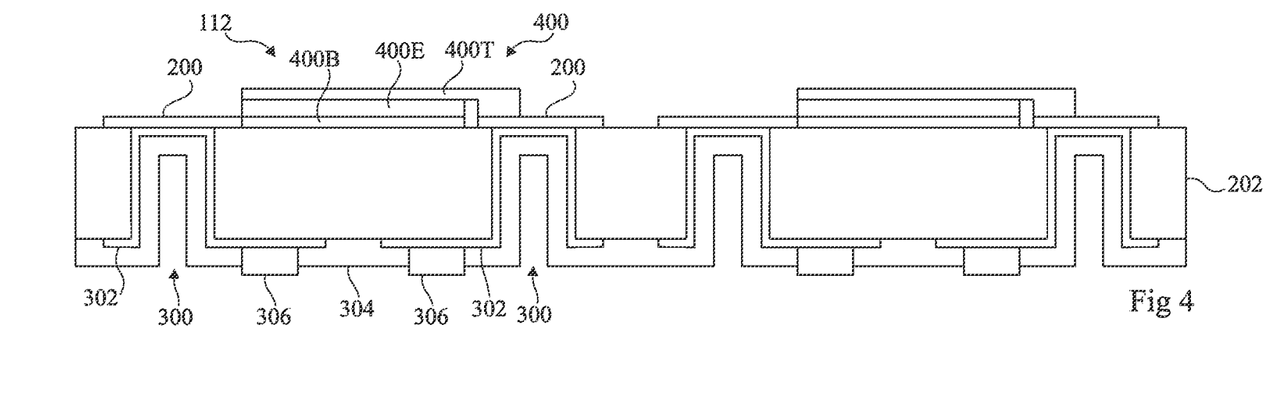
FIG. 4 is a partial simplified cross-section view illustrating still another step of the implementation mode of the method of manufacturing the culture plate of FIG. 1.

FIG. 4 is a partial simplified cross-section view illustrating still another step of the implementation mode of the method of manufacturing the culture plate 100 of FIG. 1, carried out from the structure such as described in relation with FIG. 3.

During this step, light source array 112 is formed on the upper surface side of substrate 202.

According to an embodiment, each light source 112 comprises at least one organic light-emitting diode 400, or OLED. In the shown example, each light source 112 comprises a single diode 400. Each diode 400 is for example intended to emit white light.

For simplification, each diode 400 is symbolized in FIG. 4 by a stack comprising an emissive layer 400E interposed between a lower electrode 400B and an upper electrode 400T. In the shown example, the lower electrode 400B of each diode 400 is on top of and in contact with the upper surface of substrate 202.

In practice, diodes 400 may have a more complex structure. As an example, each diode 400 may in particular comprise one or a plurality of additional layers (not shown) such as:
- an electron injection layer (EIL);
- an electron transport layer (ETL);
- a hole injection layer (HIL); and
- a hole transport layer (HTL).

In the shown example, the lower and upper electrodes 400B and 400T of each organic light-emitting diode 400 respectively contact different portions of power supply and control circuits 200. This for example enables to apply distinct electric potentials to lower electrode 400B and to upper electrode 400T. In the shown example, the lower and upper electrodes 400B and 400T of each diode 400 are connected to distinct pads 306 via different vias 300.

As an example, the lower electrode 400B of each diode 400 reflects the light emitted by layer 400E while upper electrode 400T is transparent or semi-transparent. Layer 400E for example has a transmittance greater than 10%. In the shown example, organic light-emitting diodes 400 are so-called top emission diodes.

An implementation mode where each light source 112 comprises a single diode 400 emitting white light has been described in relation with FIG. 4. As a variant, each light source 112 comprises a plurality of organic light-emitting diodes 400, for example three organic light-emitting diodes 400 intended to respectively emit:
- red light, in other words an electromagnetic radiation having a wavelength for example in the range from 610 nm to 700 nm;
- green light, in other words an electromagnetic radiation having a wavelength for example in the range from 500 nm to 570 nm; and
- blue light, in other words an electromagnetic radiation having a wavelength for example in the range from 450 nm to 490 nm.

In the case where each light source 112 comprises a plurality of light-emitting diodes 400, each diode 400 is preferably individually controllable. As an example, each diode 400 belonging to a same light source 112 is controllable independently from the other diodes 400 of the considered light source 112, and independently from the diodes 400 forming part of the other light sources 112 of plate 100.

An advantage linked to the use of organic diodes lies in the fact that this enables to obtain a small spectral emission dispersion, for example in the order of from 10 nm to 100 nm. This dispersion for example results from the structure of organic diodes 400. Biological substance 106 can thus be excited in limited wavelength ranges.

Figure 5:
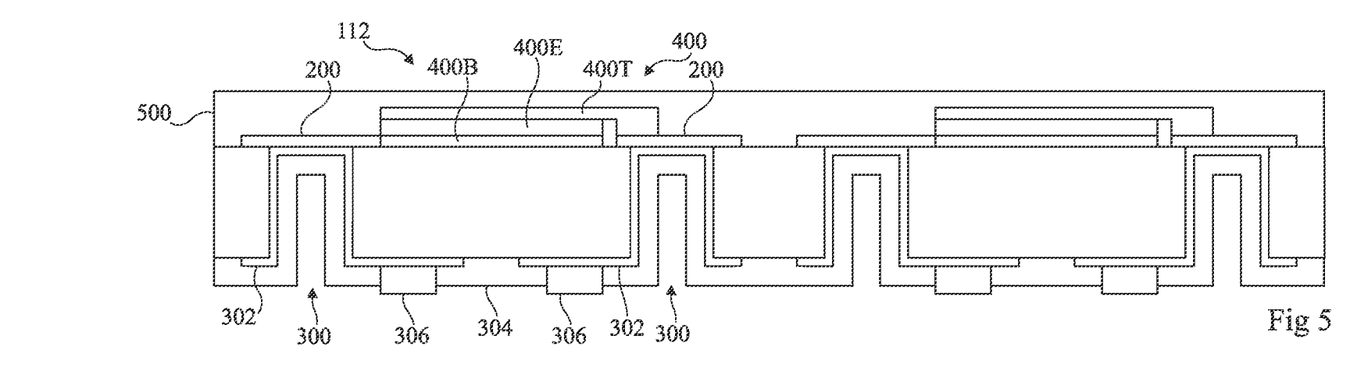
FIG. 5 is a partial simplified cross-section view illustrating still another step of the implementation mode of the method of manufacturing the culture plate of FIG. 1.

FIG. 5 is a partial simplified cross-section view illustrating still another step of the implementation mode of the method of manufacturing the culture plate 100 of FIG. 1, carried out from the structure such as described in relation with FIG. 4.

During this step, the upper surface of the structure is coated with a transparent planarization layer 500.

In the shown example, transparent planarization layer 500 particularly totally covers power supply and control circuits 200 as well as organic light-emitting diodes 400. Layer 500 forms a hard coat.

According to an embodiment, layer 500 is made of a photocrosslinkable organosilicon material. As an example, layer 500 is based on a material known under trade name HARDRISE of POLYRISE or a biocompatible resin. More generally, layer 500 is made of a biocompatible material. In practice, layer 500 is for example obtained by the implementation of a sol-gel-type method. Layer 500 for example has a thickness in the range from 1 μm to 10 μm.

Although this is not shown, an encapsulation layer of organic light-emitting diodes 400 may be deposited on the upper surface side of substrate 202 prior to the deposition of layer 500.

Figure 6:
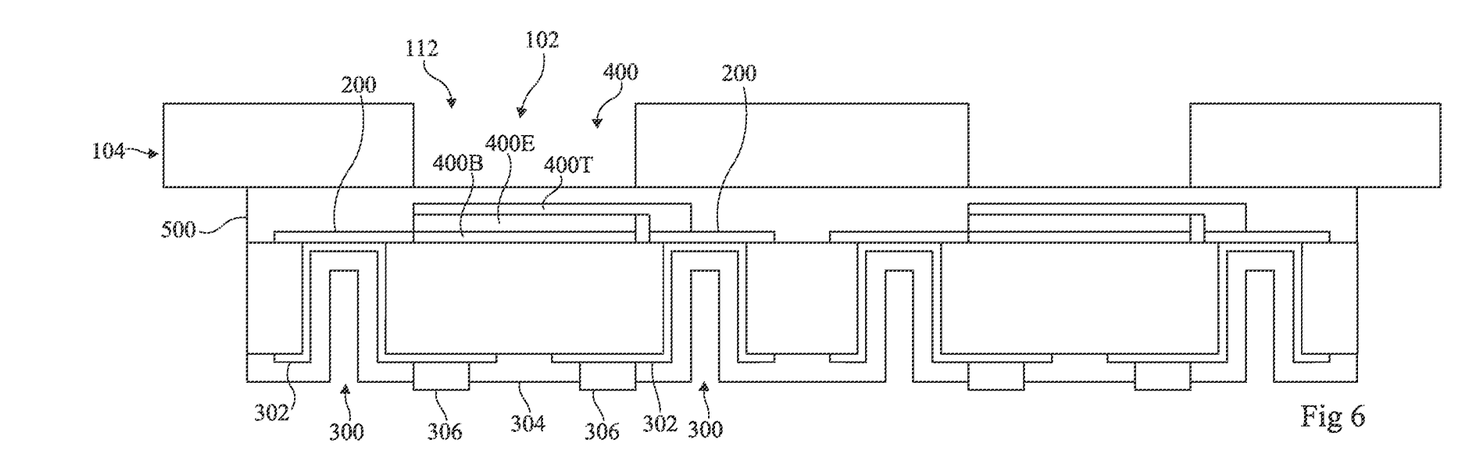
FIG. 6 is a partial simplified cross-section view illustrating still another step of the implementation mode of the method of manufacturing the culture plate of FIG. 1.

FIG. 6 is a partial simplified cross-section view illustrating still another step of the implementation mode of the method of manufacturing the culture plate 100 of FIG. 1, carried out from the structure such as described in relation with FIG. 5.

During this step, the array of wells 102 is formed.

In practice, layer 104 is for example deposited over the entire surface of the structure. Wells 102 are then formed to expose portions of planarization layer 500 located vertically in line with each light source 112. In the shown example, the bottom of each well 102 is formed by an upper surface portion of layer 500.

Figure 7:
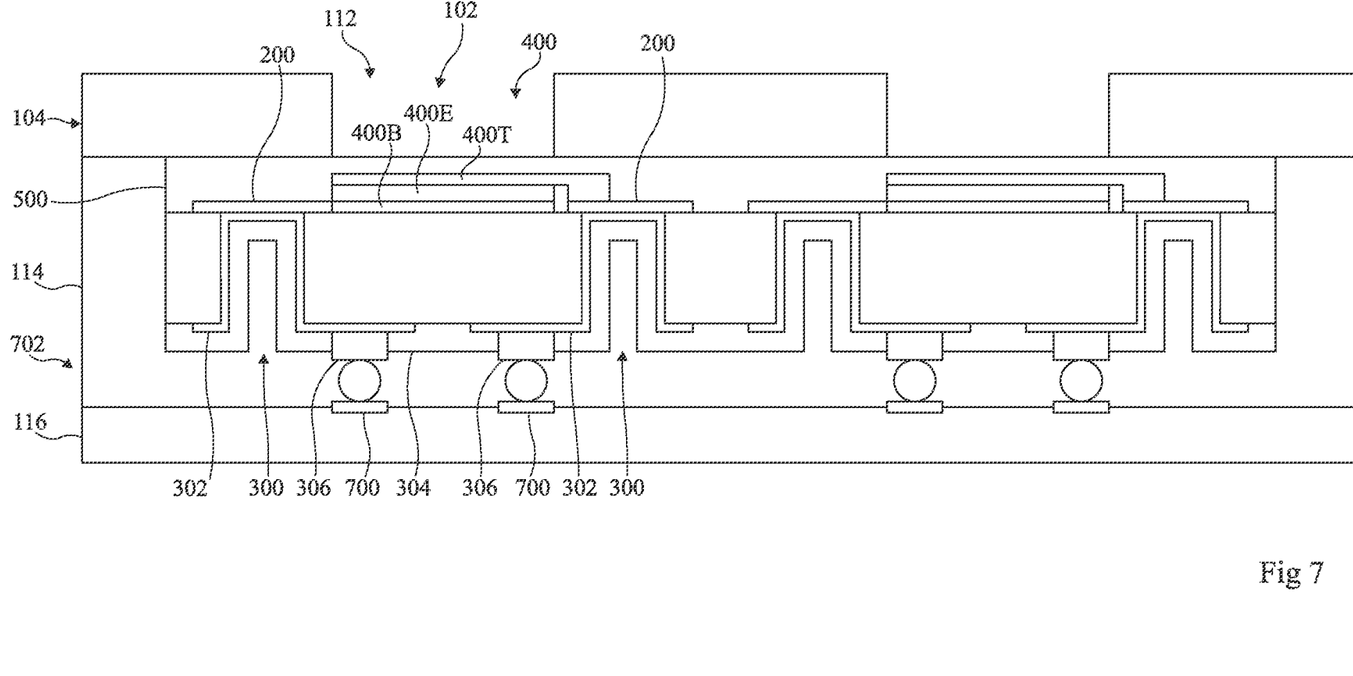
FIG. 7 is a partial simplified cross-section view illustrating still another step of the implementation mode of the method of manufacturing the culture plate of FIG. 1.

FIG. 7 is a partial simplified cross-section view illustrating still another step of the implementation mode of the method of manufacturing the culture plate 100 of FIG. 1, carried out from the structure such as described in relation with FIG. 6.

During this step, the structure is linked to printed circuit board 116 and filling layer 114 is formed.

Each pad 306 located on the lower surface side of substrate 202 is for example connected to a pad 700 located on the upper surface side of board 116. As an example, an array of solder balls 702 enables to form the connection between pads 306 and pads 700.

In the shown example, layer 114 coats the lateral surfaces of layer 500, of substrate 202, and of layer 304. Layer 114 further fills the free volume vertically delimited by the upper surface of board 116 and by the lower surface of layer 304. Generally, layer 114 is deposited so as to protect pads 306, solder balls 702, and pads 700 against oxidation.

An advantage of culture plate 100 lies in the fact that each light source 112 is separated from the bottom of well 102 to which it is associated by a distance shorter than 10 μm. Advantage is here taken from the integration of light sources 112 in culture plate 100 to decrease the distance between the bottom of each well 102 and the associated diodes 400. This for example enables to maximize the illumination to which the cells of the substance 106 present in well 102 are submitted, particularly as compared with a configuration where light sources of same power as sources 112 would be placed under a usual culture plate.

Another advantage of culture plate 100 lies in the fact that organic light-emitting diodes 400 cause a lighter heat release than that which would be obtained by for example using inorganic light-emitting diodes. This for example enables to limit risks of degradation of the biological substance 106 contained in wells 102 under the effect of the heat released during the emission of light by diodes 400.

Another advantage of culture plate 400 lies in the fact that electric connections located on the upper surface of substrate 202 are transferred onto the lower surface of substrate 202 by means of through vias 300. This enables, in particular, to protect circuits 200 against risks of aggressions which may for example result from the use of saline biological substances 106. The presence, in plate 100, of hard coat layer 500 particularly enables to avoid for biological substance 106 to come into contact with circuits 200 or diodes 400. This for example provides a greater protection than a configuration where layer 500 would be opened to expose contacting elements located on the upper surface side of substrate 202.

Another advantage of culture plate 100 lies in the fact that its use is likely to allow a time gain, for example, in the context of sequencing methods comprising steps repeated in a loop, base by base, until an entire DNA (deoxyribonucleic acid) has been sequenced. As an example, the use of culture plate 100 may allow a time gain in a case where fluorophores, associated with complementary bases grafting on the DNA strand, are each excited by a different wavelength. In this case, three colors are for example sequentially "read" to determine the location of the first three bases, a lack of emission indicating the presence of the fourth base.

Advantage may further by taken of culture plate 100 in DNA synthesis applications. As an example, the use of culture plate 100 may enable to do away with complex and time-consuming methods, such as methods comprising steps of protection and of deprotection by a microstructured mask (for example of resin type). The use of culture plate 100 in applications of this type may further enable to discard risks of errors linked, for example, to an exposure of biological substance 106 to ultraviolet light or to aggressive solvents.

Various embodiments, implementation modes, and variants have been described. Those skilled in the art will understand that certain features of these various embodiments, implementation modes, and variants, may be combined and other variants will occur to those skilled in the art. In particular, it will be within the abilities of those skilled in the art to adapt the implementation mode of the method of manufacturing plate 100 described hereabove to a case where each light source 112 comprises a plurality of diodes.

Finally, the practical implementation of the described embodiments, implementation modes, and variants is within the abilities of those skilled in the art based on the functional indications given hereabove. In particular, the forming of organic light-emitting diodes 400 is within the abilities of those skilled in the art based on the above indications.

The invention claimed is:

1. Culture plate comprising: an array of light sources formed inside and on top of a semiconductor substrate; a transparent planarization layer totally coating the array of light sources and power supply and control circuits; and an array of wells formed on said layer, each light source in the array of light sources being located vertically in line with a well; wherein a bottom of each well in the array of wells is formed by an upper surface portion of the transparent planarization layer and the array of light sources is disposed below the bottom of the array of wells; wherein the transparent planarization layer includes a biocompatible material; wherein each light source comprises at least one organic light-emitting diode; wherein each light source in the array of light sources comprises a respective independent control circuit; wherein the array of light sources is located on a side of a first surface of the substrate, opposite to a second surface of the substrate comprising connection pads; wherein connection pads are connected to the first surface of the substrate by through vias by an array of solder balls, to pads of a printed circuit board for powering and controlling the light sources.

2. Plate according to claim 1, wherein said layer is made of a photocrosslinkable organosilicon material.

3. Plate according to claim 1, wherein said layer has a thickness in a range from 1 pm to 10 pm.

4. Plate according to claim 1, wherein the array of wells is made of polydimethylsiloxane.

5. Plate according to claim 1, wherein each light source comprises a diode intended to emit white light.

6. Plate according to claim 1, wherein each diode is individually controllable.

7. Plate according to claim 1, wherein each light source comprises three diodes intended to respectively emit red light, green light, and blue light.

8. Plate according to claim 1, wherein bottom and/or lateral walls of at least a portion of the wells of the array are functionalized.

9. Method of manufacturing a plate according to claim 1.

10. Method according to claim 9, comprising the steps of: —forming the array of light sources inside and on top of the semiconductor substrate; —coating the array of light sources with the transparent planarization layer; and —forming at the surface of said layer a well vertically in line with each light source.

11. Plate according to claim 1, wherein the biocompatible material is polydimethylsiloxane (PDMS).

12. Plate according to claim 1, wherein the biocompatible material is plastic polymer.

13. Plate according to claim 12, wherein the plastic polymer is polypropylene, polystyrene, or polycarbonate.

* * * * *

UNITED STATES PATENT AND TRADEMARK OFFICE
CERTIFICATE OF CORRECTION

PATENT NO. : 12,398,354 B2
APPLICATION NO. : 17/345154
DATED : August 26, 2025
INVENTOR(S) : Tony Maindron et al.

Page 1 of 1

It is certified that error appears in the above-identified patent and that said Letters Patent is hereby corrected as shown below:

In the Claims

Claim 3, Column 9, Line 26 please delete "1 pm to 10 pm" and insert -- 1 μm to 10 μm --.

Signed and Sealed this
Eighteenth Day of November, 2025

John A. Squires
*Director of the United States Patent and Trademark Office*